(12) United States Patent  
Fitz

(10) Patent No.: US 6,306,163 B1
(45) Date of Patent: Oct. 23, 2001

(54) ASSEMBLY FOR COLLECTING EMBOLI AND METHOD OF USE

(75) Inventor: Matthew J. Fitz, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/128,439

(22) Filed: Aug. 4, 1998

(51) Int. Cl.$^7$ .................................................. A61M 29/00
(52) U.S. Cl. ........................... 623/1.12; 606/198; 606/200
(58) Field of Search ................................. 606/1, 198, 200, 606/159, 114; 604/104, 105; 623/1, 12, 1.1, 1.11, 1.12

(56) References Cited

U.S. PATENT DOCUMENTS

| 4,619,246 | 10/1986 | Molgaard-Nielsen et al. . | |
|---|---|---|---|
| 4,662,885 | 5/1987 | DiPisa, Jr. . | |
| 4,794,928 | * 1/1989 | Kletschka | 606/159 |
| 4,969,891 | 11/1990 | Gewertz . | |
| 4,990,156 | 2/1991 | Lefebvre . | |
| 5,190,561 | * 3/1993 | Graber | 606/114 |
| 5,197,971 | * 3/1993 | Bonutti | 604/105 |
| 5,695,518 | 12/1997 | Laerum . | |
| 5,695,519 | 12/1997 | Summers et al. . | |
| 5,723,917 | 2/1998 | Taheri et al. . | |
| 5,746,767 | 5/1998 | Smith . | |
| 5,800,457 | 9/1998 | Gelbfish . | |
| 5,800,525 | 9/1998 | Bachinski et al. . | |
| 5,882,329 | 3/1999 | Williams et al. . | |
| 5,944,728 | * 8/1999 | Bates | 606/200 |

FOREIGN PATENT DOCUMENTS

| 0 701 800 | 3/1996 | (EP) . | |
|---|---|---|---|
| 2580504 | * 10/1986 | (FR) | 606/200 |

* cited by examiner

Primary Examiner—Henry J. Recla
Assistant Examiner—William Lewis
(74) Attorney, Agent, or Firm—Fulwider, Patton, Lee & Utecht, LLP

(57) ABSTRACT

An apparatus and method for treating cerebral blood vessels such as carotid arteries. The system generally includes an apparatus and method for safely and easily deploying a self-expanding stent in a vessel while preventing embolic migration using a filter.

36 Claims, 11 Drawing Sheets

ASSEMBLY FOR COLLECTING EMBOLI AND METHOD OF USE

BACKGROUND OF THE INVENTION

The present invention relates generally to the field of surgical instruments. Specifically, the present invention relates to an emboli-capture device for treating cerebral blood vessels such as carotid arteries.

Stenting and angioplasty in stenosed cerebral vessels (e.g., carotid arteries) pose risks of dislodging thrombus or friable plaque. The thrombus or plaque can become lodged in the brain or arteries and cause serious injury such as a stroke. If such embolic material is dislodged during a stenting procedure, it is necessary to collect the material before the it migrates and causes injury. A previous invention, U.S. Pat. No. 4,921,478, "Cerebral Balloon Angioplasty System," Solano et al., employs an occlusion catheter carrying a relatively large inflatable occlusion balloon to repair vessels. The balloon is capable of being formed into a funnel while simultaneously sealing a vessel and establishing retrograde blood flow. The balloon is bulky and difficult to refold and withdraw from lesions within the vessels. The withdrawal is prone to causing extensive tissue damage and dislodging more emboli. Moreover, the balloon-type system will not work effectively without a complete and perfect seal between the balloon and the vessel wall. Moreover, Solano et al. contemplates no occlusion in conjunction with the deployment of a self-expanding stent. Furthermore, although the prior art filtered the blood, sometimes excess emboli remained when the device was removed from blood vessels.

What has been needed and heretofore unavailable is a means to deliver and implant a stent in conjunction with a safe and easy-to-use device and method of use for stenting blood vessels while minimizing the risk of embolic migration. The present invention satisfies this need.

SUMMARY OF THE INVENTION

The present invention is directed to an apparatus and method for treating stenosed cerebral blood vessels such as carotid arteries. The system generally includes an apparatus and method for safely and easily deploying a self-expanding stent in a vessel while preventing embolic migration.

In a preferred embodiment, a system for percutaneously delivering a stent within a vessel while preventing embolic migration includes: a restraining sheath that is capable of both expanding and retracting whereby minimal friction is created between the restraining sheath and the stent during deployment of the stent; a filter for trapping and retaining embolic material, the filter being located relative to the restraining sheath such that the filter will trap any embolic material flowing into the restraining sheath; a stent delivery catheter having a proximal end open to atmospheric pressure and a distal end connected to a proximal end of the restraining sheath; and a stent that initially is in a collapsed state and positioned within the restraining sheath.

The filter may consist of one of many devices already in use, e.g., a strainer device comprised of a plurality of wires. The expansion of the restraining sheath may be accomplished by mechanically pushing a composite sheath using a design similar to that of an umbrella.

In another preferred embodiment, expansion of the filter may be accomplished by using a wedge and spine mechanism to open the restraining sheath from a closed position.

In another preferred embodiment, the expansion of the filter may be accomplished by releasing a plurality of bent wires that are restrained in a straightened position.

The sheath design provides optimal deployment of the self-expanding stent because the sheath both expands in a radial direction and retracts in a proximal direction simultaneously. Therefore, due to the angle of incidence created between the sheath and the stent during deployment there is a low coefficient of friction between the sheath and the stent. This is an ideal configuration for recapturing a partially deployed stent because contact is constantly maintained between the sheath and the undeployed part of the stent.

A desired site within a vessel is first accessed with the system. The restraining sheath is then deployed while being moved proximally. The restraining sheath, as it expands, forms an occlusive conical member or catch basin at a proximal end of the stent. The stent, being self-expanding, is automatically deployed as the restraining sheath expands. A temporary seal is created between the stent and the restraining sheath. An outer edge of a distal end of the restraining sheath may include a material taken from the group of materials consisting of soft plastic, rubber, and a gel, in order to ensure a proper seal between the sheath and the stent. Therefore, unlike the situation where a balloon exerts pressure on a vessel wall to cause a seal, in the present invention vessel damage is minimized.

The filter is located within the restraining sheath at the occlusion site in another embodiment.

In yet another preferred embodiment, the filter may be located within the stent delivery catheter. Alternatively, the filter may be located outside of the patient's body.

Due to the occlusion of the vessel at the proximal end of the stent, a pressure differential is created between the more distal arteries (pressurized at blood pressure plus atmospheric pressure) and a lumen of the stent delivery catheter (pressurized at atmospheric pressure). Therefore, retrograde blood flow is induced and blood and embolic particles are flushed into the filter where the embolic particles are captured.

In another preferred embodiment, a vacuum apparatus may be included in the system if the occlusion is not adequate to induce sufficient retrograde blood flow or to ensure that the maximum number of embolic particles are aspirated into the filter. The restraining sheath is then collapsed to its original size, thereby trapping any remaining embolic material. The system is then removed from the patient.

Other features and advantages of the present invention will become more apparent from the following detailed description of the invention when taken in conjunction with the accompanying exemplary drawings.

DETAILED DESCRIPTION OF THE PREFERRED EMBODIMENTS

Figure 1:
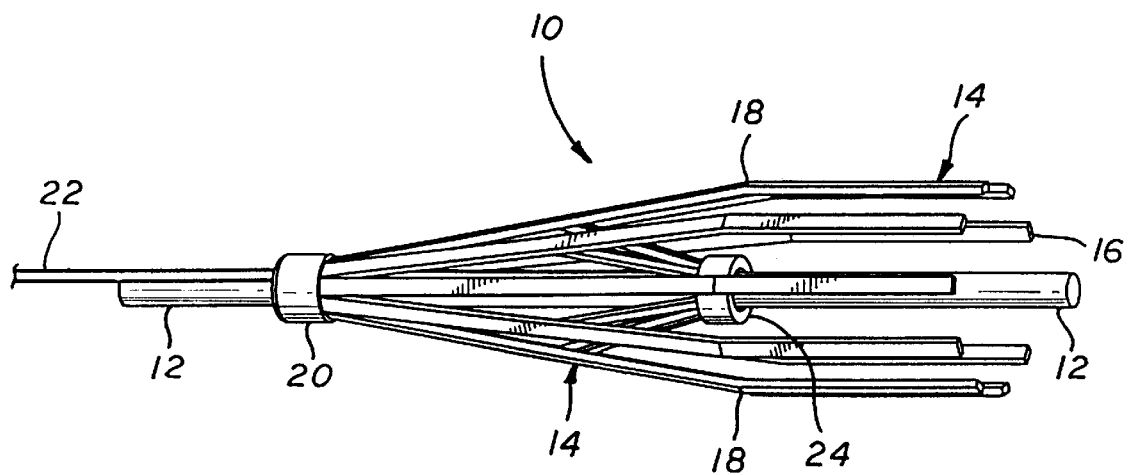
FIG. 1 is a perspective view of one embodiment, depicting in a closed position an apparatus of a composite design similar to that of an umbrella for expanding a restraining sheath wherein expansion is accomplished by mechanically pushing the sheath.
Figure 2:
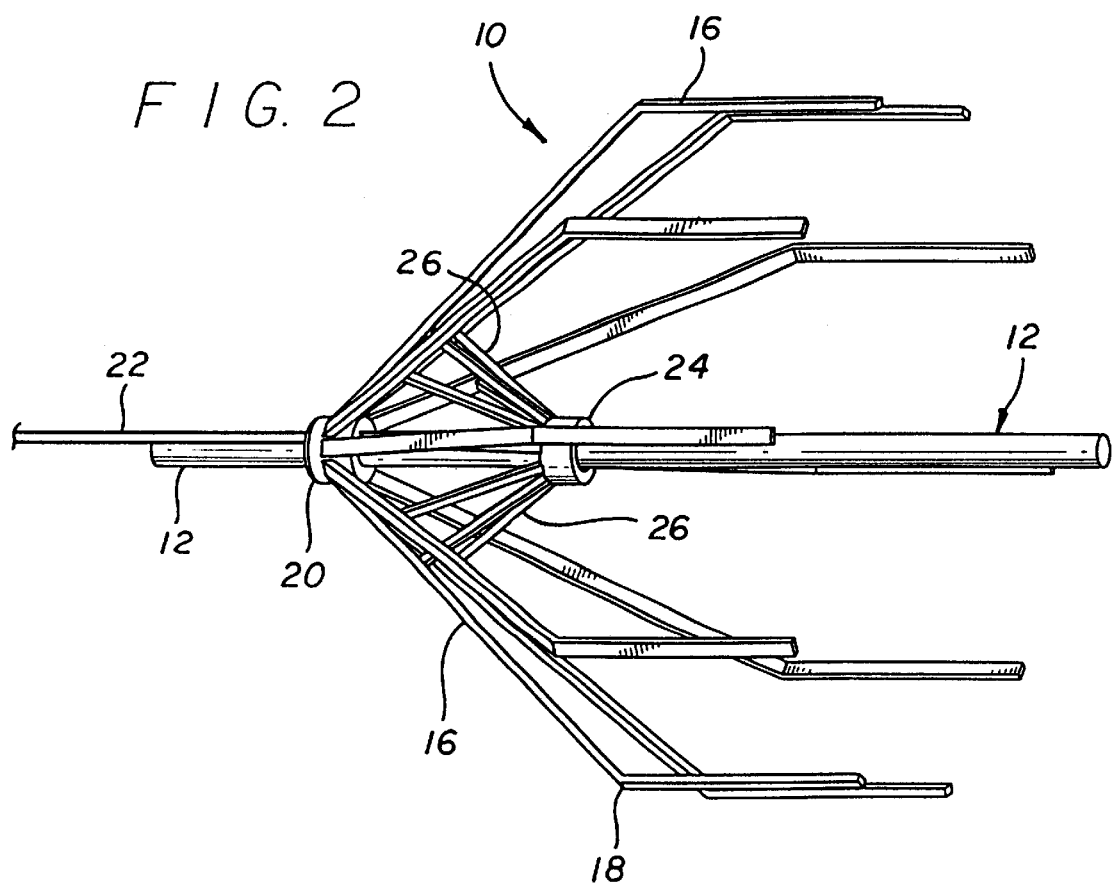
FIG. 2 is a perspective view of the apparatus of FIG. 1 depicted in an open position.

As shown in the exemplary drawings, the present invention may be embodied in various ways. Where common elements occur in more than one embodiment, the same reference numerals will be used. Referring to FIG. 1, depicting one preferred embodiment, apparatus 10 of a composite design similar to that of an umbrella for expanding a restraining sheath is shown. The restraining sheath is omitted for clarity. A stent delivery catheter 12 is coaxially positioned within apparatus 10. Expansion of the restraining sheath is accomplished by mechanically pushing the sheath via expansion of expandable cage 14. The cage 14 consists of spines 16 each of which have bend 18. The spines 16 are secured by fixed support ring 20 at the proximal end of spines 16. A distal end of control wire 22 is fixed to collar 24 that is slidably mounted about the delivery catheter. The cage is expanded by pulling the collar proximally via the control wire which causes secondary spines 26 (see FIG. 2) to press against the larger spines 16. One end of each secondary spine 26 is pivotally secured to collar 24. The opposing end of each secondary spine 26 is pivotally secured to larger spine 16. Likewise, the proximal end of each larger spine 16 is pivotally secured to the fixed control ring 20. As a result, cage 14 pushes outwardly on the sheath membrane and the sheath thus expands at a distal end and forms a catch basin.

Figure 3:
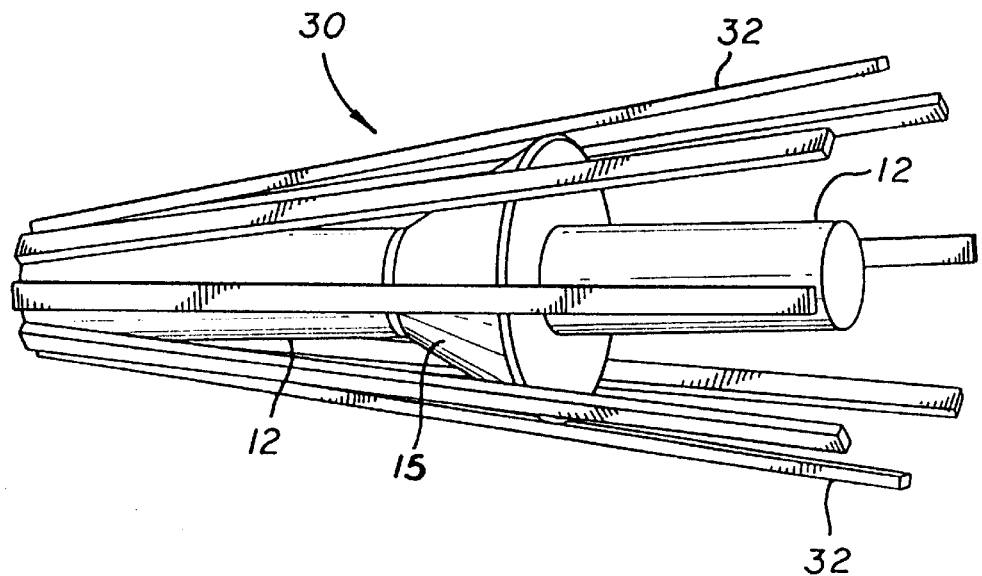
FIG. 3 is a perspective view of another embodiment depicting an apparatus in a closed position for expanding the restraining sheath wherein expansion is accomplished by using a wedge and spine mechanism to open the restraining sheath from a closed position.

In another preferred embodiment, apparatus 30 provides expansion for the sheath membrane (omitted for clarity), as shown in FIG. 3. A plurality of spines 32 project distally and function to support the sheath. The spines 32 are pivotally secured at their proximal ends to stent delivery catheter 12. Wedge 15 is slidably mounted on the stent delivery catheter and may be moved axially relative to the catheter and spines 32 by a control wire (omitted for clarity) or other means.

Figure 4:
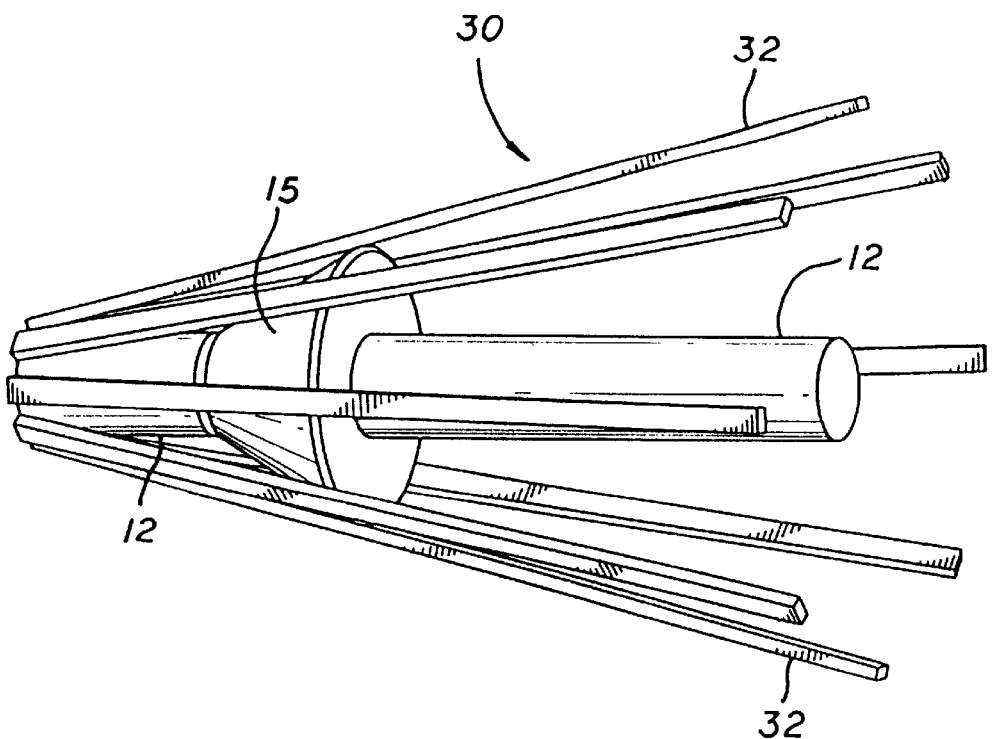
FIG. 4 is a perspective view of the apparatus of FIG. 3 in a partially expanded position.
Figure 5:
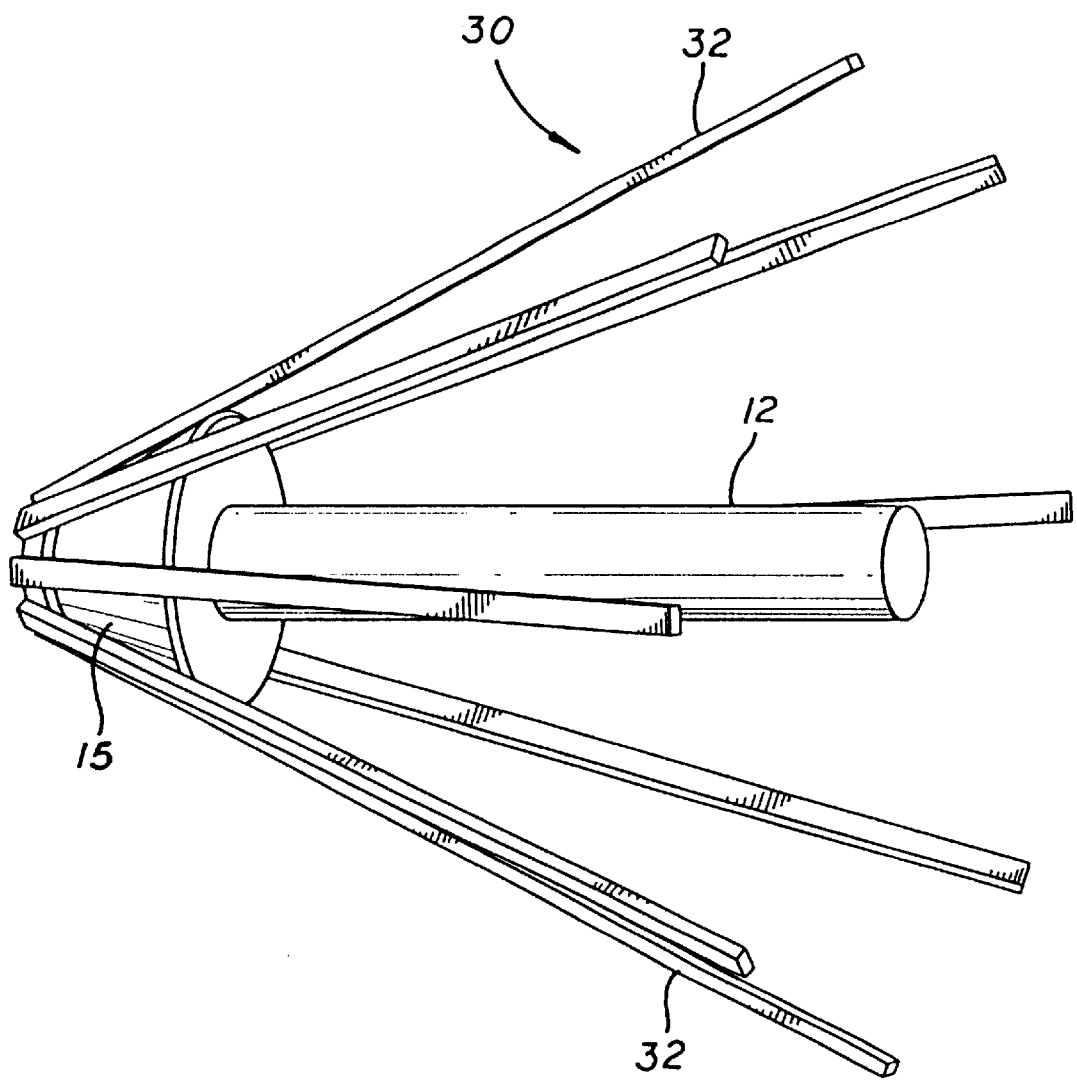
FIG. 5 is a perspective view of the apparatus of FIG. 3 in a fully expanded position.

As shown in FIG. 4, when wedge 15 is moved proximally relative to the spines, the wedge forces the spines to protrude outwardly in a radial direction. FIG. 5 depicts the spines in a fully expanded position. The wedge has been moved as far as possible in a proximal direction.

Figure 6:
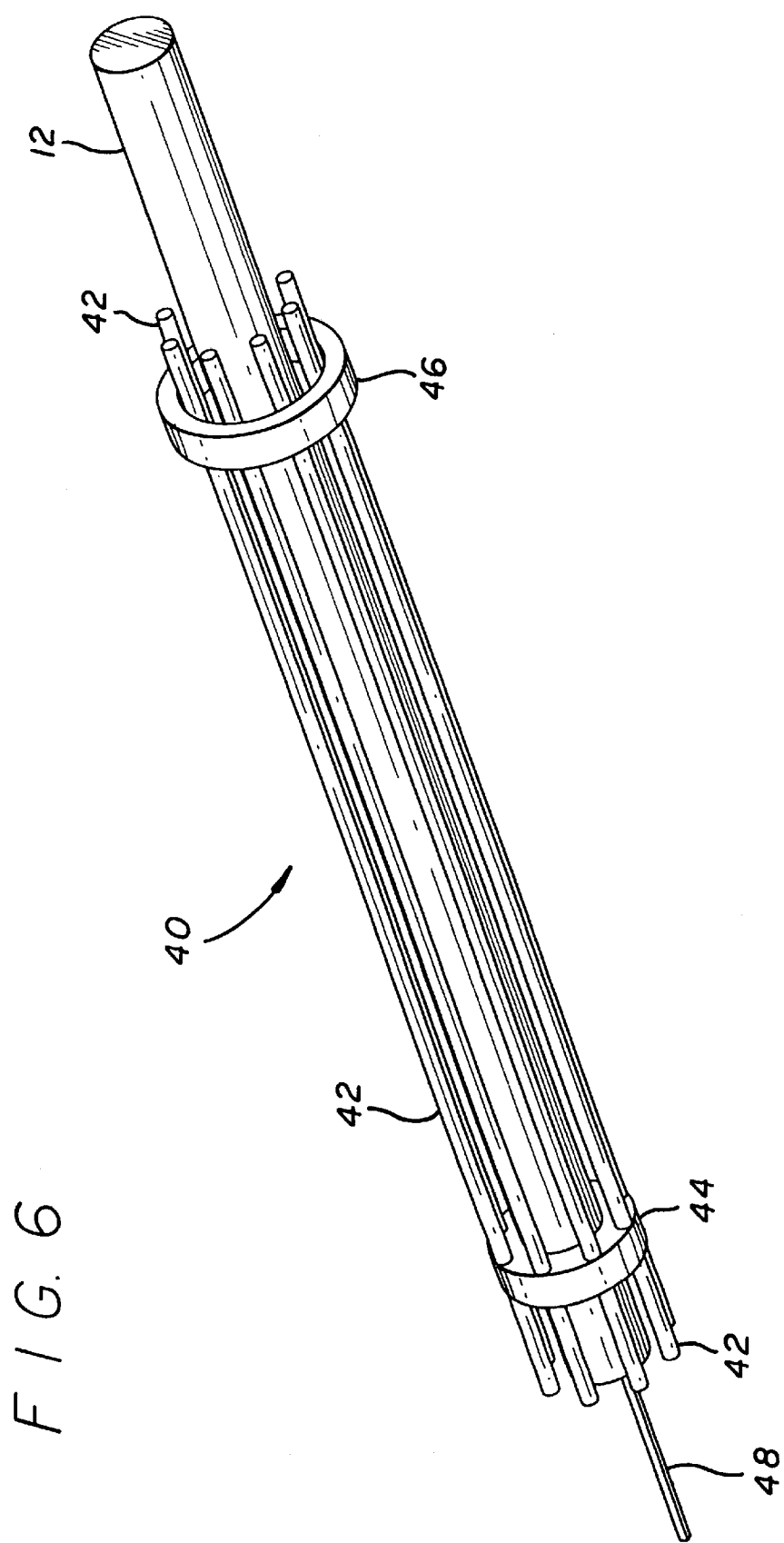
FIG. 6 is a perspective view of another preferred embodiment depicting an apparatus in a closed position for expanding the restraining sheath wherein expansion is accomplished by releasing bent wires that are restrained in a straightened position.

As shown in FIG. 6, apparatus 40 for expanding the sheath membrane (omitted for clarity) provides yet another preferred embodiment. A plurality of bent wires 42 are restrained in a straightened position by fixed restraint ring 44 at a proximal end of apparatus 40 and slidably mounted restraint ring 46 at a distal end of the apparatus. The slidably mounted restraint ring is initially positioned at the distal ends of wires 42. Catheter 12 is coaxially positioned within wires 42 and rings 44,46. A second control wire 48 is attached to the slidably mounted restraint ring.

Figure 7:
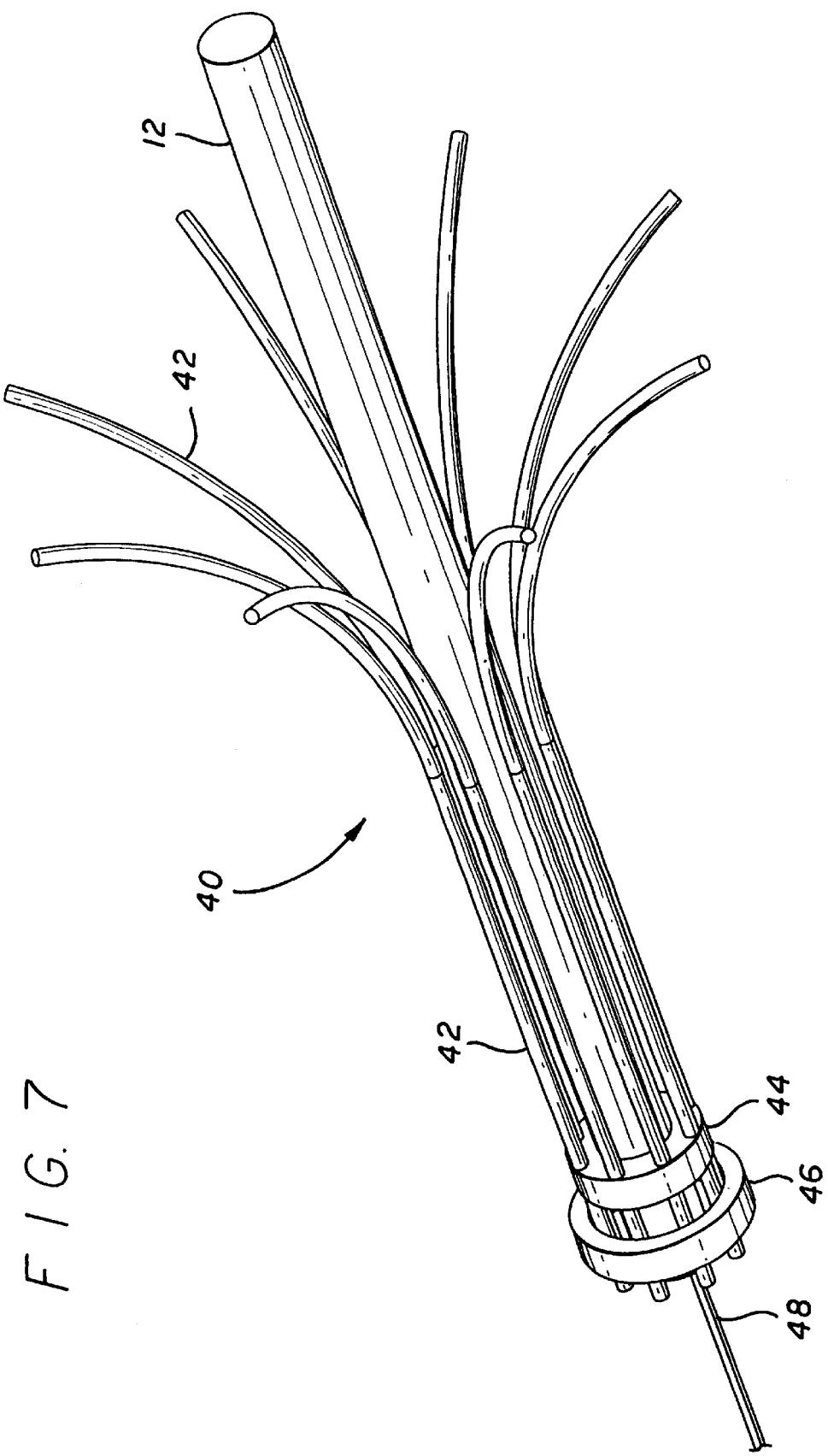
FIG. 7 is a perspective view of the apparatus of FIG. 6 in a fully expanded position.

Referring to FIG. 7, the slidably mounted restraint ring 46 has been moved proximally via the second control wire. The wires 42 have thus been released and have sprung into their resting bent positions. This action serves to fully expand a restraining sheath.

Figure 8:
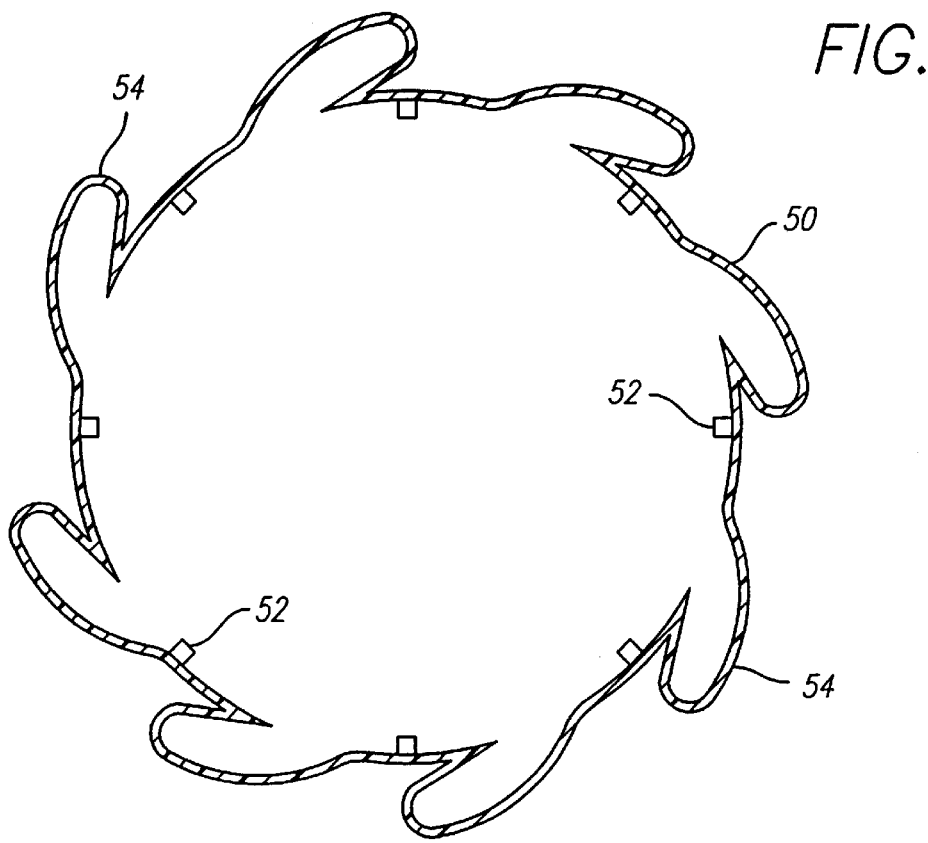
FIG. 8 is a cross-sectional view of a restraining sheath in a closed position.

Turning to FIG. 8, restraining sheath 50 is depicted and is supported by spines 52, or alternatively wires. The restraining sheath in a closed position may consist of folds 54. An alternative to providing folds 54 is to construct a restraining sheath of a material that is capable of being stretched in a radial direction. This alternative would require less material but would require more force to expand the material in a radial direction than would be required if folds were implemented. A restraining sheath may be formed from a material selected from the group of materials consisting of polyethylene, polyester and polyamide. The material, which has a low coefficient of friction, may be obtained in varying grades of softness.

Figure 9:
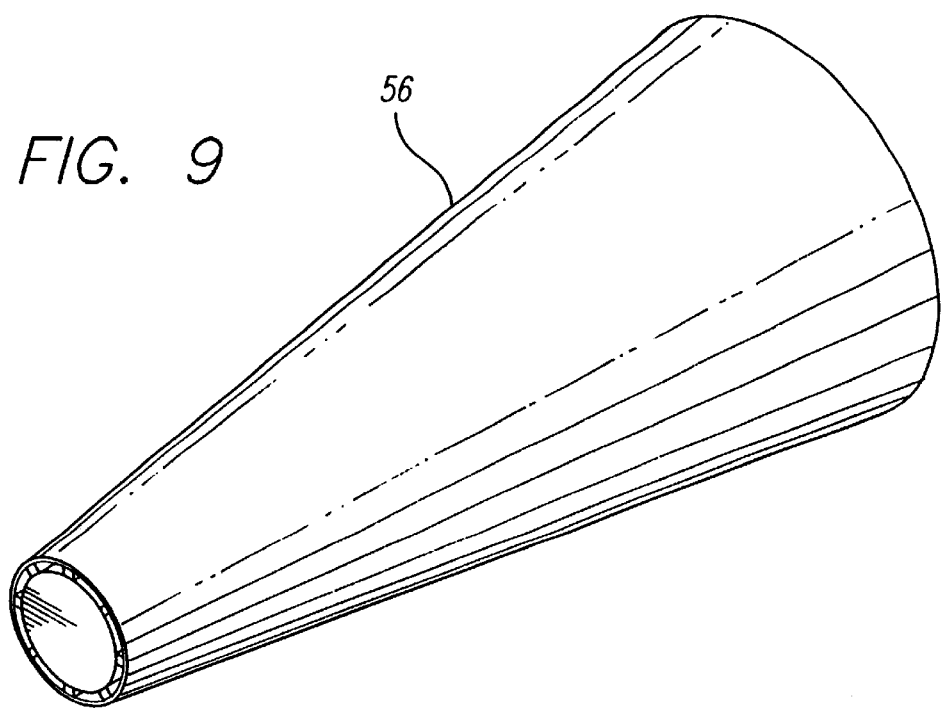
FIG. 9 is a perspective view of a restraining sheath that has been partially expanded by the apparatus of FIG. 3.

As shown in FIG. 9, restraining sheath 56 may be expanded by apparatus 30 of FIG. 3 such that the diameter at the distal end is larger than the diameter at the proximal end.

Figure 10:
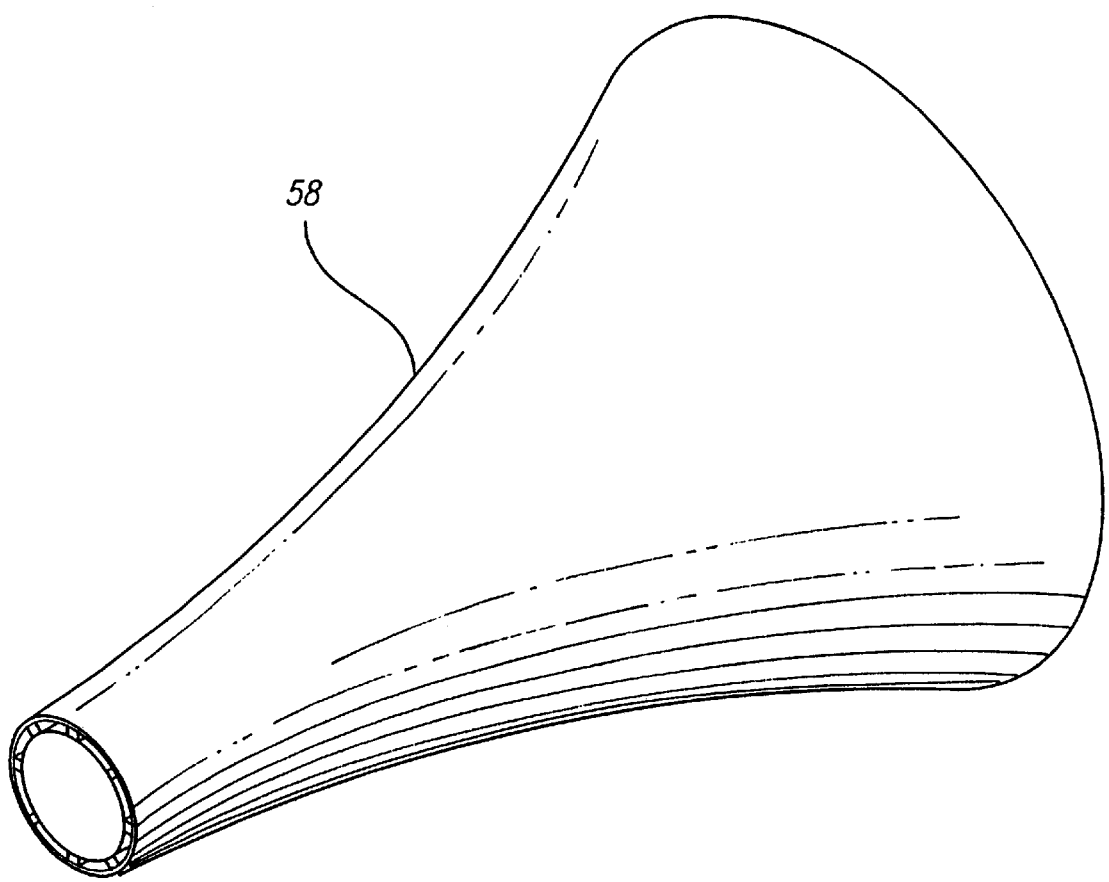
FIG. 10 is a perspective view of a restraining sheath that has been partially expanded by the apparatus of FIG. 6.

Turning to FIG. 10, restraining sheath 58 may be expanded by the apparatus of FIG. 6 such that the diameter at the distal end is larger than the diameter at the proximal end.

The sheath design provides optimal deployment of the self-expanding stent because the sheath both expands in a radial direction and retracts in a proximal direction simultaneously. Therefore, due to the angle of incidence created between the sheath and the stent during deployment, there is a low coefficient of friction between the sheath and the stent. This is an ideal configuration for recapturing a partially deployed stent because contact is constantly maintained between the sheath and the undeployed part of the stent.

Figure 11:
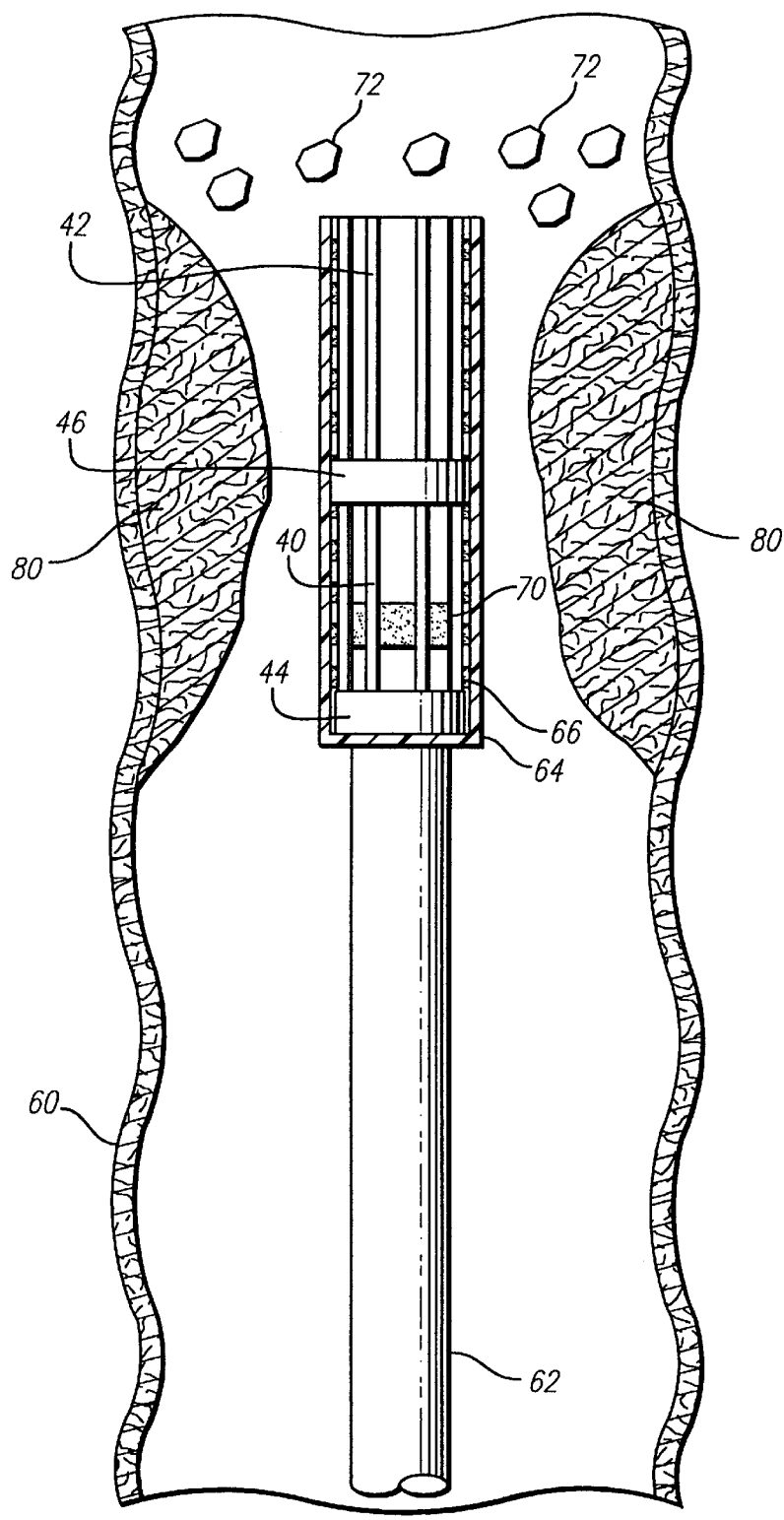
FIG. 11 is an elevational view of the present invention, partially in cross-section, after advancement to a desired vessel site and just prior to commencement of stent deployment.
Figure 12:
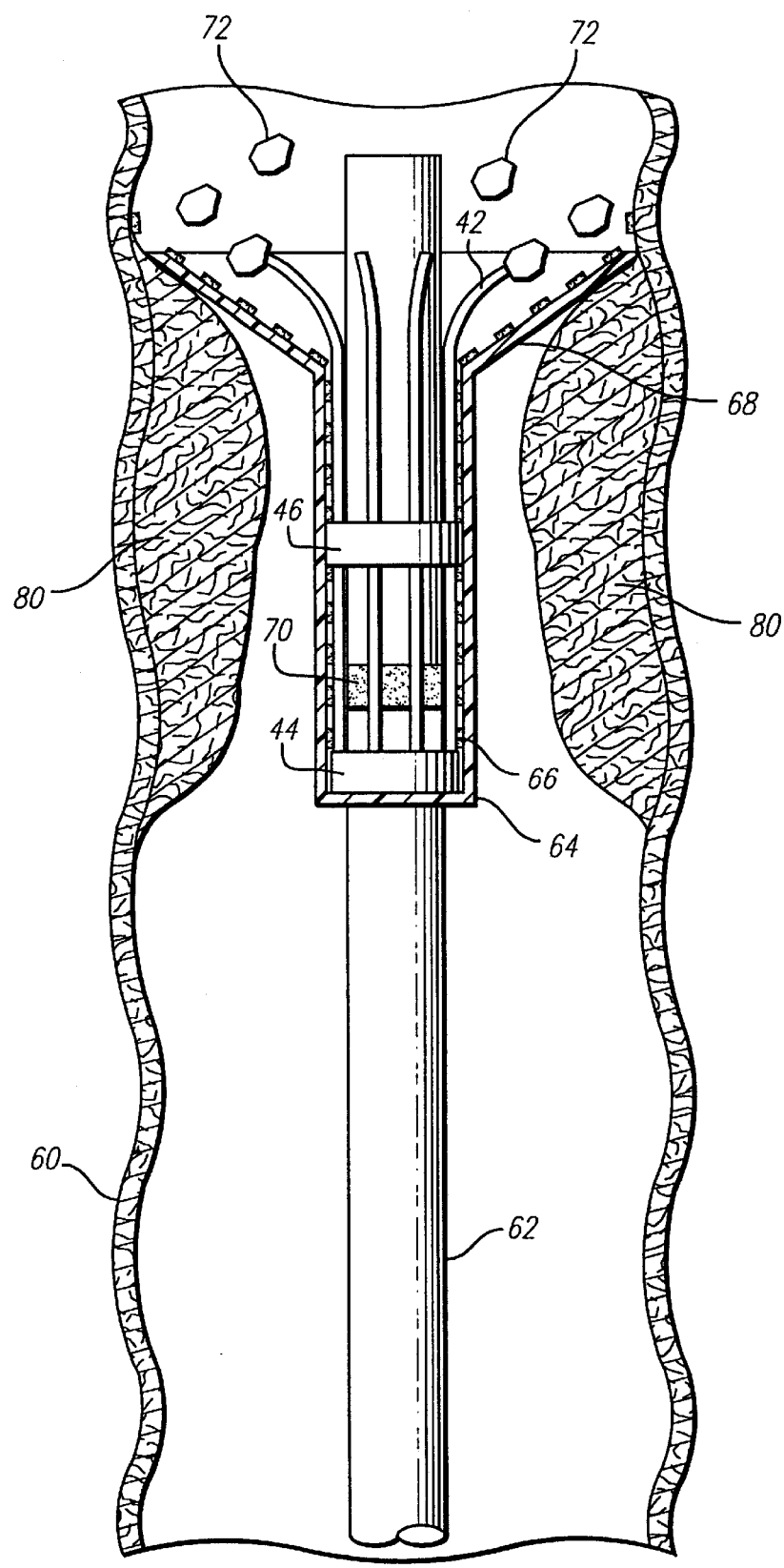
FIG. 12 is an elevational view, partially in cross-section, depicting the present invention during stent deployment.
Figure 13:
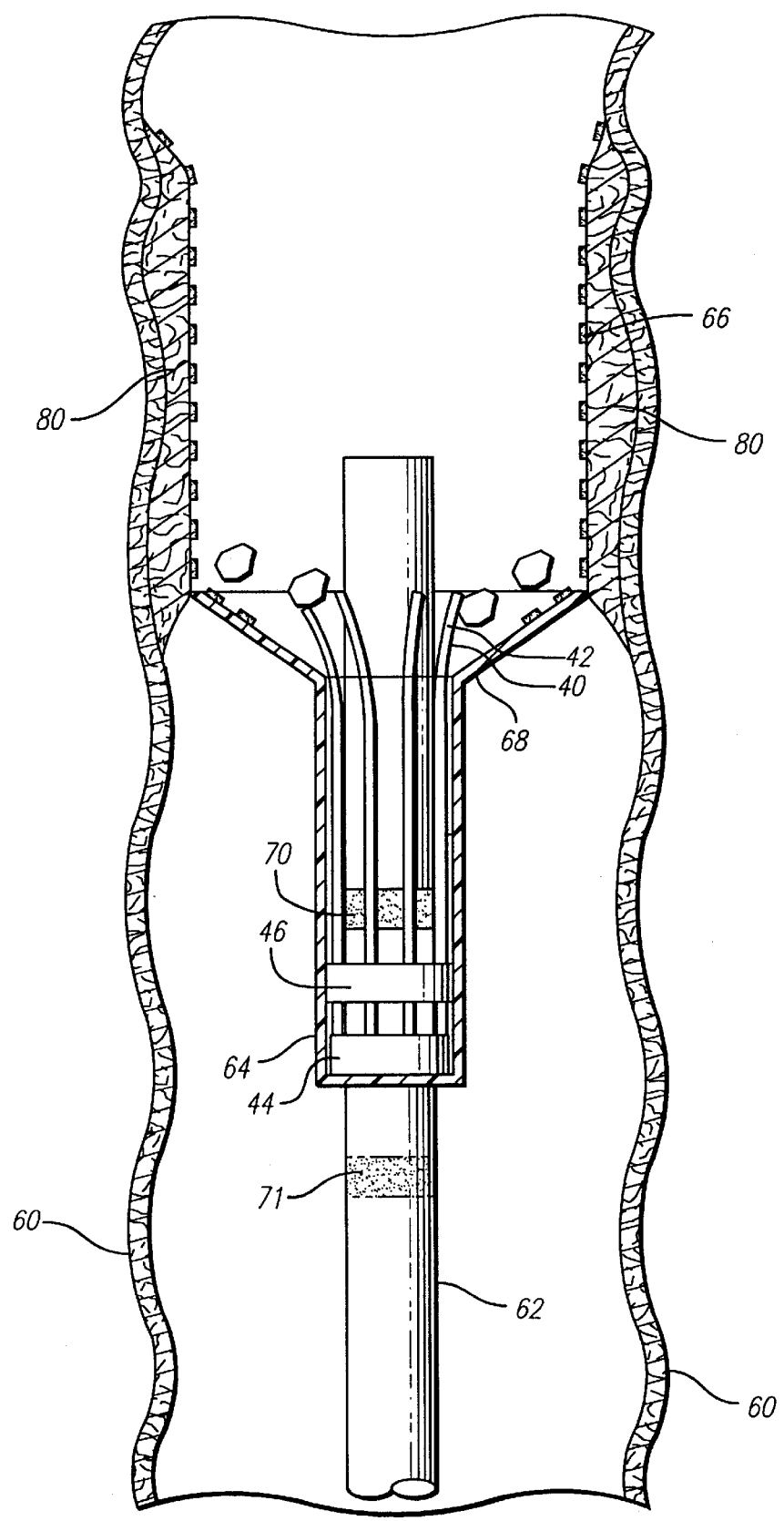
FIG. 13 is an elevational view, partially in cross-section, depicting the present invention after the stent has been fully deployed.

Turning to FIGS. 11–13, in a preferred method, a desired site within vessel 60 is first accessed with the system, via a percutaneous technique. A stent delivery catheter 62 has its proximal end open to atmospheric pressure and its distal end running into the proximal end of restraining sheath 64. Self-expanding stent 66 is initially in a collapsed state and partially disposed within the restraining sheath. The restraining sheath 64 is attached to and deployed by an apparatus such as the apparatus 40 shown in FIGS. 6–8. A plurality of bent wires 42 are restrained in a straightened position by a fixed restraint ring 44 at the proximal end of the apparatus 40 and a slidably mounted restraint ring 64 near the distal end of the apparatus. A control wire (not shown) or other means for moving the restraint ring 46 can be attached to the slidable mounted restraint ring 46 to enable the plurality of bent wires 42 to be deployed. As the bent wires 42 are deployed, the restraining sheath 64 is in turn deployed within the patient's vasculature. The restraining sheath is then deployed, and as it expands, forms occlusive conical member 68 or catch basin at the proximal end of the stent. The stent, being of the self-expanding type, is automatically deployed as the restraining sheath expands. A temporary seal is created between the stent and the restraining sheath. The outer edge of the distal end of restraining sheath 64 may include a material consisting of soft plastic, rubber, or a gel, in order to ensure a proper seal between the sheath and the stent. Therefore, unlike the situation where a balloon exerts pressure on a vessel wall to cause a seal, in the present invention vessel damage is minimized. As is shown in FIG. 12, when the restraining sheath 64 is expanded by the outward movement of the wires 42, it also is simultaneously retracted back to allow a portion of the self-expanding stent 66 to expand and contract a portion of the stenosis 80 formed in the vessel 60. The self-expanding stent 60 will begin to expand and contact more area of the stenosis 80 as the restraining sheath 64 is retracted via the action of the wires 42. It also should be appreciated that the delivery catheter 62 may have to be retracted back away from the stenosis 80, as is shown in FIG. 13, to allow the entire self-expanding stent 66 to be deployed across the stenosis 80 since the length of retraction of the restraining sheath 64 may be somewhat limited by the action of the particular apparatus used to expand and retract the sheath 64.

A filter 70 for trapping and retaining embolic material or particles 72 is located within the lumen of the stent delivery catheter and relative to restraining sheath 64 such that the filter will trap any embolic material flowing into the restraining sheath. Such filters are known in the art and may include a strainer device comprised of a plurality of wires. The filter may be located within the restraining sheath at the occlusion site in one embodiment. In another embodiment, filter 70 may be located within the lumen of the stent delivery catheter 62, at a location outside of the restraining sheath 64 as shown in phantom in FIG. 13. In yet another preferred embodiment, the filter may be placed within the lumen of the catheter at a location outside of the patient's body (not shown).

Due to the occlusion of vessel 60 at the proximal end of stent 66, a pressure differential is created between the more distal arteries (pressurized at blood pressure plus atmospheric pressure) and a lumen of the stent delivery catheter (pressurized at atmospheric pressure). Therefore, retrograde blood flow is induced and blood and embolic particles are flushed into filter 70 where the embolic particles are collected. An opening in the delivery catheter (not shown) distal to the filter provides an entrance to the lumen of the catheter which draws the embolic material into the opened restraining sheath 64 and into the filter 70.

Figure 14:
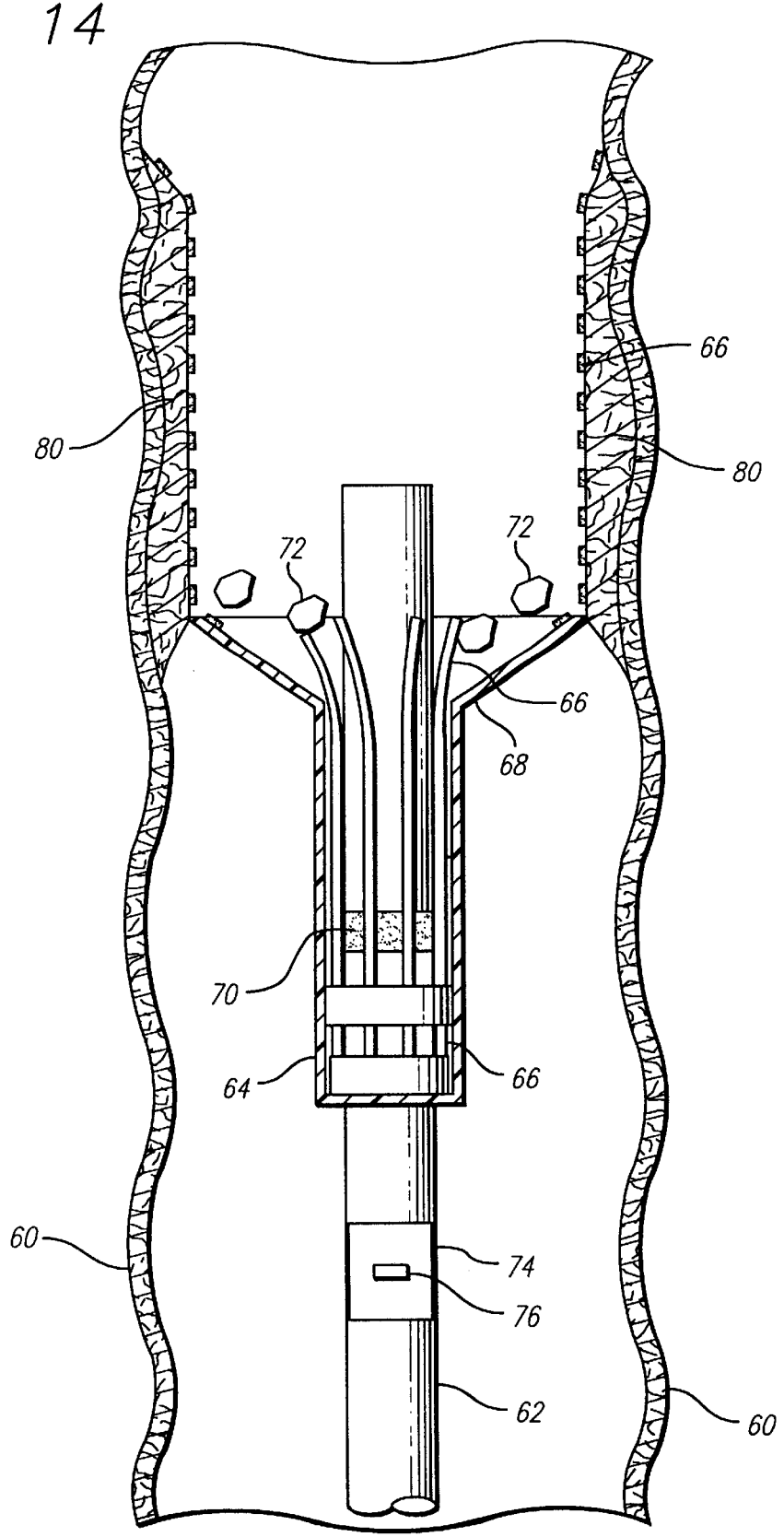
FIG. 14 is an elevational view, partially in cross-section, depicting the resent invention after the stent has been fully deployed, including an optional vacuum apparatus.

Turning to FIG. 14, in another preferred embodiment an aspiration system consisting of vacuum device 74 with optional valve 76 may be included in the system if the occlusion is not adequate to induce sufficient retrograde blood flow or to ensure that the maximum number of embolic particles 72 are aspirated into filter 70. Alternatively, in another embodiment, an aspiration system consisting of a luer lock (not shown) capable of accepting a syringe may be used. The restraining sheath 64 is then collapsed to its original size, thereby trapping any remaining embolic material or particles 72. The restraining sheath 64 is collapsed by simply moving the slidable mounted restraint ring 46 distally to retract the plurality of bent wires 42. The system is then removed from the patient. Thus, a self-expanding stent is deployed safely and easily without the risk of embolic migration.

While the invention has been illustrated and described herein in terms of its use as a safe and easy-to-use apparatus and method for treating blood vessels while minimizing the risk of embolic migration, it will be apparent to those skilled in the art that the invention can be used in other instances. Other modifications and improvements may be made without departing from the scope of the invention.

What is claimed is:

1. A system for delivering a stent within a body vessel for minimizing the risk of embolic migration, comprising:
    a restraining sheath adapted for expanding and retracting within the body vessel such that minimal friction exists between the restraining sheath and the stent during deployment of the stent;
    a filter for collecting and retaining embolic material, the filter being located relative to the restraining sheath so that the filter collects any embolic material flowing into the restraining sheath;
    a stent delivery catheter having an internal lumen with a proximal end open to atmospheric pressure and a distal opening extending into the restraining sheath and a region for mounting the stent thereto the filter being located within the internal lumen; and
    wherein the stent is initially mounted on the stent delivery catheter in a low profile collapsed state and is positioned within the restraining sheath.

2. The system of claim 1, wherein the restraining sheath is formed from a material that has a low coefficient of friction.

3. The system of claim 2, wherein the restraining sheath expands to form a catch basin.

4. The system of claim 2, wherein an outer edge of a distal end of the restraining sheath includes a material taken from the group of materials consisting of soft plastic, rubber, and a gel, thereby ensuring a seal between the sheath and the stent.

5. The system of claim 2, wherein the restraining sheath includes a plurality of folds for expanding from a closed position to an open position.

6. The system of claim 2, wherein the restraining sheath is formed from an elastic material so that the restraining sheath can be stretched from a closed to an open position.

7. The system of claim 2, wherein expansion of the restraining sheath may be accomplished by an apparatus including an expandable cage having a plurality of first spines, each of the first spines including a bend and being pivotally secured by a fixed support ring at a proximal end, the apparatus further including a plurality of secondary spines, each of the secondary spines being pivotally secured at a proximal end to one of each of the first spines and being pivotally secured at a distal end to a slidably mounted collar, the cage pushing outwardly on the sheath when the collar is moved proximally.

8. The system of claim 2, wherein a wedge and a spine mechanism move the restraining sheath from a closed position to an open position.

9. The system of claim 2, wherein one or more restrained spring elements are provided to expand the restraining sheath.

10. The system of claim 9, wherein a plurality of bent wires are associated with the restraining sheath, the bent wires being restrained in a straightened collapsed position which when released causes the restraining sheath to expand.

11. The system of claim 10, further including a restraint ring for retaining the bent wires in a straightened position.

12. The system of claim 11, further including a fixed support ring for supporting the bent wires at a proximal end.

13. The system of claim 1, wherein the restraining sheath is formed from a material selected from the group of materials consisting of polyethylene, polyester, polyamide, peba, silicone, rubber, nylon and elastomers.

14. The system of claim 1, wherein the restraining sheath is formed from a material that may be obtained in varying grades of softness.

15. The system of claim 1, wherein the filter is located in the internal lumen at a position within the restraining sheath.

16. The system of claim 1, wherein the filter is located in the internal lumen at a position proximal to the restraining sheath.

17. The system of claim 1, wherein the filter is located in the internal lumen at a position outside of the body of a patient.

18. The system of claim 1, further including an aspiration system for aspirating embolic material into the stent delivery catheter.

19. The system of claim 18, wherein the aspiration system attaches the stent delivery catheter by a luer lock fitting.

20. The system of claim 19, wherein the luer lock is capable of accepting a syringe for facilitating the aspiration of embolic material into the stent delivery catheter.

21. The system of claim 18, wherein the aspiration system includes a vacuum apparatus for inducing retrograde blood flow.

22. The system of claim 21, wherein the vacuum apparatus includes a valve for facilitating rapid activation of the vacuum apparatus.

23. The system of claim 1, further including a self-expanding stent.

24. A system for delivering a stent within a body vessel and capturing embolic material released into the fluid flow of the vessel, comprising:
   a stent delivery catheter having a restraining sheath adapted for expanding and retracting within the body vessel attached thereto; the stent delivery catheter including an internal lumen having a proximal end open to atmospheric pressure and a distal opening extending into the restraining sheath to attain at least some retrograde fluid flow into the lumen when the restraining sheath is expanded within the body vessel, the delivery catheter having a region for mounting a stent thereto which extends within the restraining sheath; and
   a mechanism for expanding and retracting the restraining sheath.

25. The system of claim 24, further including a filter element located within the internal lumen of the catheter to trap embolic material which may be drawn into the lumen.

26. The system of claim 24, further including a filter element located within the internal lumen of the catheter to trap embolic material which may be drawn into the lumen.

27. The system of claim 24, further including an aspiration system for aspirating embolic material into the stent delivery catheter.

28. The system of claim 27, wherein the aspiration system includes a vacuum apparatus for inducing retrograde fluid flow.

29. The system of claim 28, wherein the vacuum apparatus includes a valve for facilitating rapid activation of the vacuum apparatus.

30. The system of claim 24, wherein the aspiration system attaches the stent delivery catheter by a luer lock fitting.

31. The system of claim 30, wherein the luer lock is capable of accepting a syringe for facilitating the aspiration of embolic material into the stent delivery catheter.

32. The system of claim 24, further including a self-expanding stent.

33. A method for deploying a self-expanding stent within a vessel while simultaneously preventing the migration of embolic material, utilizing a system including a restraining sheath, a filter, a stent delivery catheter having a proximal end open to atmospheric pressure and a distal end running into a proximal end of the restraining sheath, and a self-expanding stent, comprising the steps of:
   accessing a desired site within the vessel with the system;
   deploying the restraining sheath while moving the sheath proximally, thereby forming a catch basin and simultaneously deploying and implanting the self-expanding stent, the catch basin occludes the vessel at a proximal end of the stent, thereby inducing retrograde blood flow through the filter;
   collapsing the restraining sheath and collecting any remaining embolic material; and
   removing the system from the patient.

34. A method for deploying a self-expanding stent within a vessel while simultaneously capturing a resultant emboli, utilizing a system including a restraining sheath, a filter, a stent delivery catheter having a proximal end open to atmospheric pressure and a distal end running into a proximal end of the restraining sheath, a vacuum apparatus, and a self-expanding stent, comprising the steps of:
   accessing a desired site within the vessel with the system;
   deploying the restraining sheath while moving the sheath proximally, thus causing the formation of a catch basin and the automatic deployment of the stent, whereby the catch basin occludes the vessel at a proximal end of the stent, thereby inducing retrograde blood flow through the filter;
   activating the vacuum apparatus to maximize the aspiration of embolic material into the filter;
   collapsing the restraining sheath to its original size, thus collecting any remaining embolic material; and
   removing the system from the patient.

35. A method of creating a pressure differential in a vessel to collect embolic material by creating a substantially atraumatic seal across a lesion within the vessel while preventing embolization.

36. The method of claim 35, further including activating a vacuum apparatus to maximize the amount of embolic material that is aspirated into a filter.

* * * * *